United States Patent [19]

Holt et al.

[11] Patent Number: 5,285,521
[45] Date of Patent: Feb. 8, 1994

[54] AUDIBLE TECHNIQUES FOR THE PERCEPTION OF NONDESTRUCTIVE EVALUATION INFORMATION

[75] Inventors: Amos E. Holt; Kent D. Polk; Richard A. Cervantes, all of San Antonio, Tex.

[73] Assignee: Southwest Research Institute, San Antonio, Tex.

[21] Appl. No.: 678,741

[22] Filed: Apr. 1, 1991

[51] Int. Cl.$^5$ .............................................. G10L 9/00
[52] U.S. Cl. ................................................ 395/2.79
[58] Field of Search .................... 381/51–53; 395/2.79; 29/4

[56] References Cited

U.S. PATENT DOCUMENTS

| | | | |
|---|---|---|---|
| 3,672,210 | 6/1972 | Cressman et al. | 29/04 |
| 3,813,926 | 6/1974 | Stubbeman | 29/04 |
| 3,962,909 | 6/1976 | Lund | 29/04 |
| 4,088,030 | 5/1978 | Iversen et al. | 29/04 |
| 4,098,130 | 7/1978 | Coffey et al. | 29/04 |
| 4,193,306 | 3/1980 | Flaherty et al. | 29/04 |
| 4,269,065 | 5/1981 | Clark | 1/00 |
| 4,428,685 | 1/1984 | Lemelson et al. | 381/51 |
| 4,563,770 | 1/1986 | Lemelson et al. | 381/51 |

*Primary Examiner*—Michael R. Fleming
*Assistant Examiner*—Michelle Doerrler

[57] ABSTRACT

A method and apparatus for utilizing the sound and pattern recognition capabilities of the human auditory system, which takes information contained in typical instrumentation signals in the form of amplitude, frequency, and time characteristics, and converts this information into sound qualities and characteristics which are recognizable by the human listener. The method and apparatus digitizes the analog amplitude, frequency, and time information, and selects appropriate sound characteristics into which it may encode this information in standardized form that is recognizable to the human listener. The method allows for the testing or inspection of materials using nondestructive evaluation techniques in a manner that allows the tester to interpret the information provided by the testing system, either exclusively through his auditory senses, or through his auditory senses in conjunction with visual indicators.

12 Claims, 5 Drawing Sheets

AUDIBLE TECHNIQUES FOR THE PERCEPTION OF NONDESTRUCTIVE EVALUATION INFORMATION

BACKGROUND OF THE INVENTION

1. Field of the Invention

This invention relates generally to devices and methods for perceiving quantitative and qualitative information. This invention relates more specifically to audible methods and techniques for perceiving information provided by instrumentation used in the nondestructive evaluation of materials.

2. Description of Related Art

Nondestructive evaluation (NDE) technologies such as ultrasonics, acoustic emission, electromagnetics, radiography, and others, all generally rely on some form of visual presentation of the inspection information to allow for the human interpretation of the data. It is usually up to the test operator to rapidly view and translate the graphic information presented to him in order to acquire an understanding of the physical characteristics of the material under test and to properly control the progression of the analysis.

One of the most common NDE technologies is the utilization of ultrasonic signals for the detection of cracks and other irregularities in materials. The information provided by ultrasonic NDE methods is typically in the form of a visual display on a cathode ray tube or on a computer video display screen. The operator of such a system must interpret the visual displays of frequencies, amplitudes, and time in a manner that allows him to locate, and to some extent describe, the characteristics of the cracks or other irregularities found within the material under test.

In ultrasonic NDE, the material being tested may be scanned by a test operator with transducers that receive and/or transmit an ultrasonic signal. The receivers may be coincidentally located with the transmitter or may be separate elements on the same or an adjacent surface. The operator, therefore, must correlate what he sees on a display with the location of the transducers at any particular instant, and with the expected propagation paths of the signal in the material. Subtle variations in the display and the rapidity with which the display changes often prevent the operator/technician from visually interpreting all of the information being provided.

Figure 2:
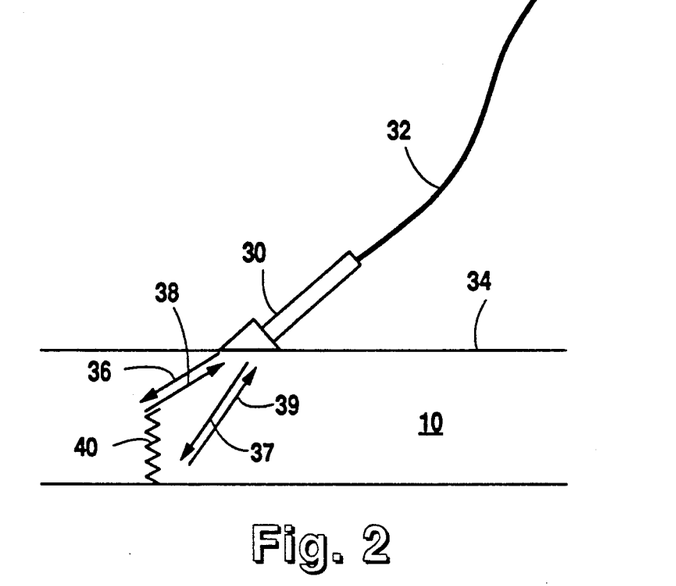
FIG. 2 is a schematic diagram of the prior art Tip Diffraction method of detecting cracks in material, and determining their size.
Figure 3:
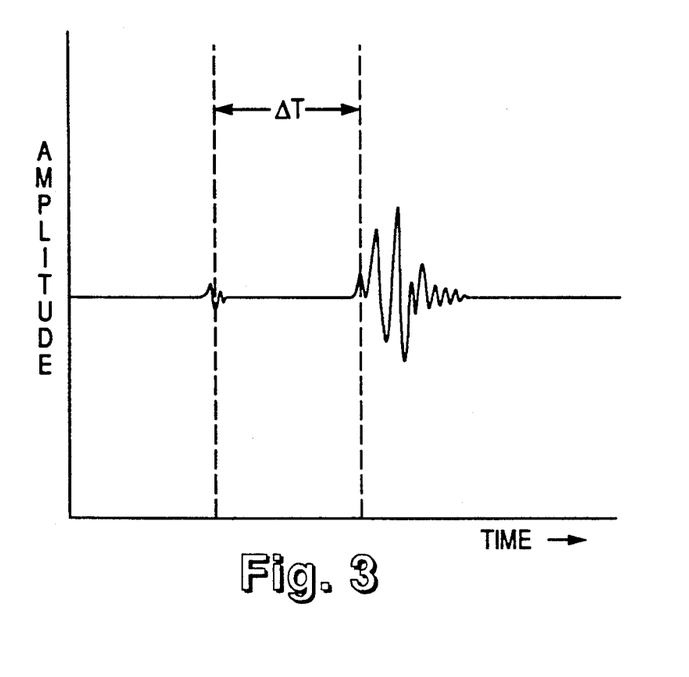
FIG. 3 is a typical display of visual information provided by the ultrasonic method shown in FIG. 2.

Ultrasonic evaluation is one of the more frequently utilized NDE technologies, and is representative of the NDE technologies to which the present invention may apply. Ultrasonic methods are widely used to detect and determine the depth or size of cracks and other flaws within otherwise homogenous materials. One ultrasonic crack sizing method, called the Tip Diffraction method, relies on the detection of two time separated signals. A schematic diagram of a typical application of the Tip Diffraction method is seen in FIG. 2. A visual display of the reflected and diffracted signals received from such a crack is shown in FIG. 3. Normally a strong reflected signal is received from the base of the crack and a smaller diffracted signal is created by the tip of the crack. The time difference between the occurrences of these two signals is directly related to the depth of the crack by common physical and trigonometric relations. An inspector can visually use this nondestructive inspection information to detect and size a crack by observing the signal information received and presented in a traditional NDE manner.

Figure 4:
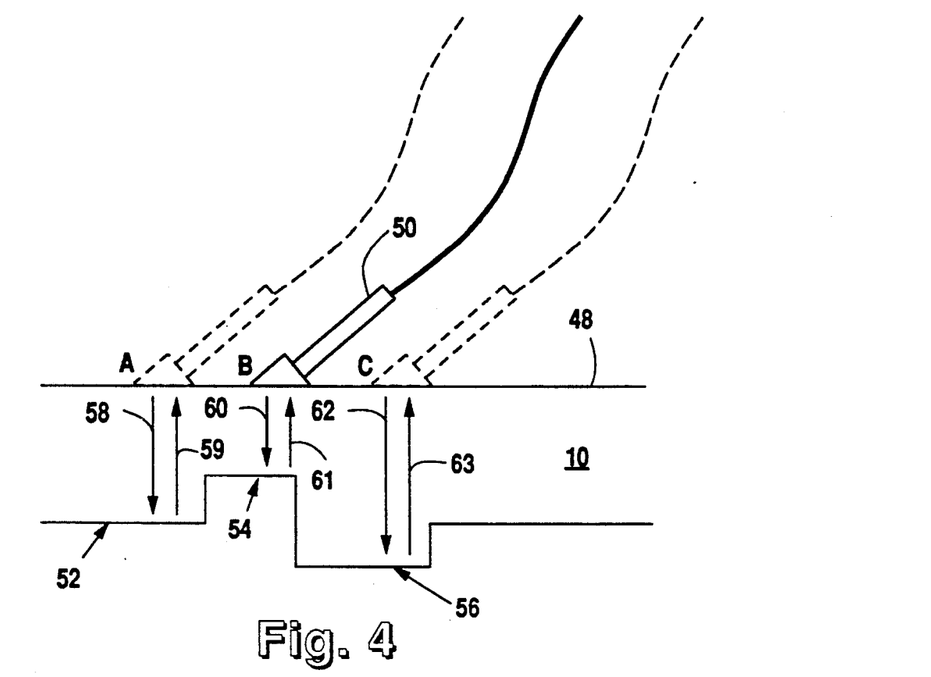
FIG. 4 is a schematic diagram of a prior art ultrasonic method of determining wall thicknesses in a material.
Figure 5:
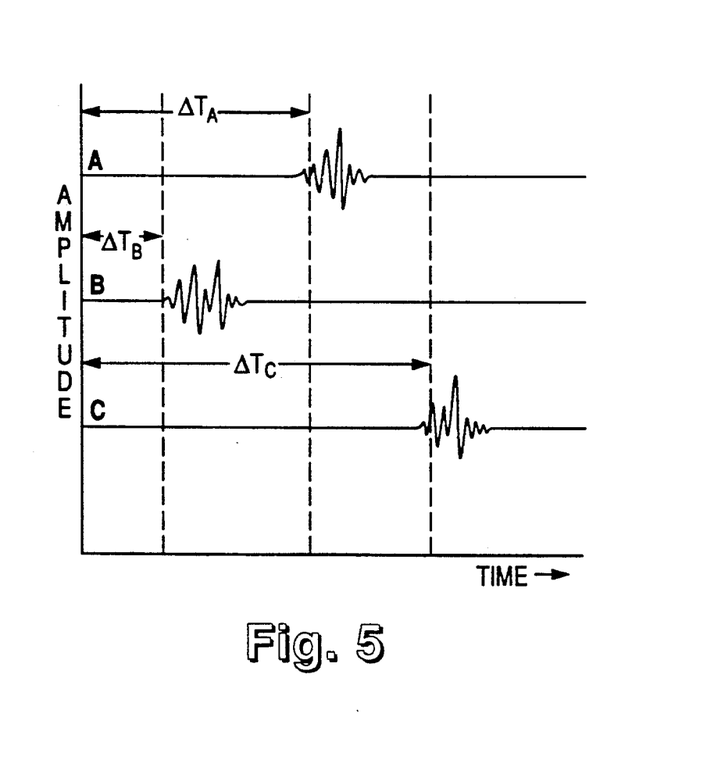
FIG. 5 is a typical display of visual information provided by the ultrasonic method shown in FIG. 4.

Another common use of ultrasonic technology is the determination of material wall thicknesses where an inspector does not have access to both sides of the wall, as in pipelines, aircraft structures, or power plant components. An ultrasonic pulse may be directed through the thickness dimension of the material, and be reflected back by the opposite wall to be received by the transducer. A typical signal representation which shows signals for three different thicknesses is depicted in FIG. 5. FIG. 4 schematically shows the configuration of an apparatus suitable for this method of determining wall thicknesses. The thickness of the material directly related to the ultrasonic signal's transit time through the material, and the velocity of sound in the material. This technique is also useful for (but is not limited to) detecting internal flaws such as material inclusions, delaminations, cracks, porosity, etc.

Whereas much emphasis in the NDE field has been placed on creating various means for extracting information from materials, very little emphasis has been placed on creating suitable methods for test operators to rapidly and easily interpret the information provided by these high tech means. Most of the existing ultrasonic and other NDE technologies rely almost exclusively on the presentation of the information in graphic form. The greatest extent to which the utilization of the human auditory system is involved has been to incorporate audible alarm systems that may be triggered when some material characteristic is detected that is out of a predetermined set of bounds. Beyond utilizing alarms for detection purposes, there is very little, if any, application of the human auditory system to the analysis of the characteristics presented in the information gathered using NDE technologies.

In general, NDE technologies rely on the utilization of non-destructive acoustic and electromagnetic waves and fields to remotely sense and describe physical properties of materials without altering their functional or structural integrity. Though disparate in nature, both acoustic and electromagnetic waves and fields have common describable parameters that can be easily translated into corresponding parameters for an electrical signal. The process of converting the sound waves and electromagnetic waves and fields into electrical signals whose amplitudes, frequencies, and time characteristics are directly related to the amplitudes, frequencies and time characteristics associated with the sound waves and electromagnetic waves is quite common. This is the aspect of NDE technology that has received the most attention since its development. Very little progress has been made, however, in taking these electrical signals generated by NDE transducers and/or sensors, and converting them into a form, other than visual, that can be readily interpreted by a human test operator.

It is not uncommon to view a human individual's most valuable sensory device as the human optical system. This is perhaps why most NDE information is provided to a test operator in graphic form, because of the assumption that the human optical system will be the best means for assessing and interpreting the NDE information. overlooked in the NDE field, and perhaps lesser understood, is the ability of the human auditory system to receive and interpret information. While much progress has been made in the NDE field to gather evermore detailed information about the characteristics of a material, not enough attention has been focused on the development of a systematic approach to allow the NDE test operator to interpret that information with his additional physical senses. It is this latter focus that forms the basis of the present invention.

SUMMARY OF THE INVENTION

The capability of the human mind to interpret audible information is generally taken for granted or overlooked in most scientific endeavors. In an effort to exploit the use of the human sense of hearing, a unique combination of techniques and technologies are described in the present invention for the audible perception and recognition of NDE information.

The human ear routinely identifies and correlates subtle changes in the sound environment which relate to specific actions, conditions, or other events to which it is exposed. For example, in an automobile, a driver can isolate and correlate a clattering noise to an engine problem, while at the same time, hearing the sounds of surrounding traffic, road noise, and music from the radio. These human capabilities can also be put to use in interpreting information associated with nondestructive evaluations, such as ultrasonic inspection. Since most NDE applications utilize the visual inspection of electronic signals, it would be helpful to translate the signal information into audible sound that can be used to aid in the recognition or detection of flaws or other pertinent conditions. A combination of audible and visual indications would assist an inspector to more quickly and effectively perform a nondestructive inspection.

The present invention employs the human aural system in the fields of metrics and pattern recognition to assist in the measurement of time and distance information, and the recognition of specific conditions in materials under evaluation. There are a number of different combinations of the properties of sound that may be utilized to create and "encode" this information. Among these properties are pitch, loudness, damping, direction, duration, repetition, and rest.

It is therefore an object of the present invention to provide methods and devices for interpreting quantitative and qualitative signal information by way of the auditory senses.

It is a further object of the present invention to provide methods and devices for interpreting signal information using the auditory senses that allows the interpreter to more rapidly recognize information and information patterns.

It is a further object of the present invention to provide methods and devices for interpreting signal information that utilizes the auditory senses, and which allows the interpreter to detect minor variations in the information that might otherwise go unnoticed in more common visual signal displays.

It is a further object of the present invention to provide methods and devices for interpreting quantitative and qualitative information provided by nondestructive testing equipment by utilizing the auditory senses in a manner that increases an inspector's speed and sensitivity to material irregularities and dimensions.

It is a further object of the present invention to provide methods and devices of interpreting quantitative and qualitative information provided by ultrasonic testing systems, which allows a technician to characterize material irregularities and dimensions of a substance being tested with or without referring to a visual display for such information.

In fulfillment of these and other objects, the present invention provides methods and devices for receiving analog signal information, which contains time, frequency, and amplitude variables, and transforming this information into sound waves which have encoded within them the signal information in a form that is recognizable and detectable to the human auditory system. The present invention utilizes electronic signal information representative of time, amplitude, and frequency, and converts this information into recognizable tones, timbres, aural patterns, and other sound characteristics that have been standardized with the operator/technician. The present invention may be utilized alone or in conjunction with standard visual means for interpreting data so as to increase the sensitivity and responsiveness of an inspector or operator of information providing equipment. The present invention is particularly applicable to nondestructive testing systems, wherein rapid and minute changes in signal information can be easily overlooked and/or confused with background signal interference.

DETAILED DESCRIPTION OF THE PREFERRED EMBODIMENT

Figure 1:
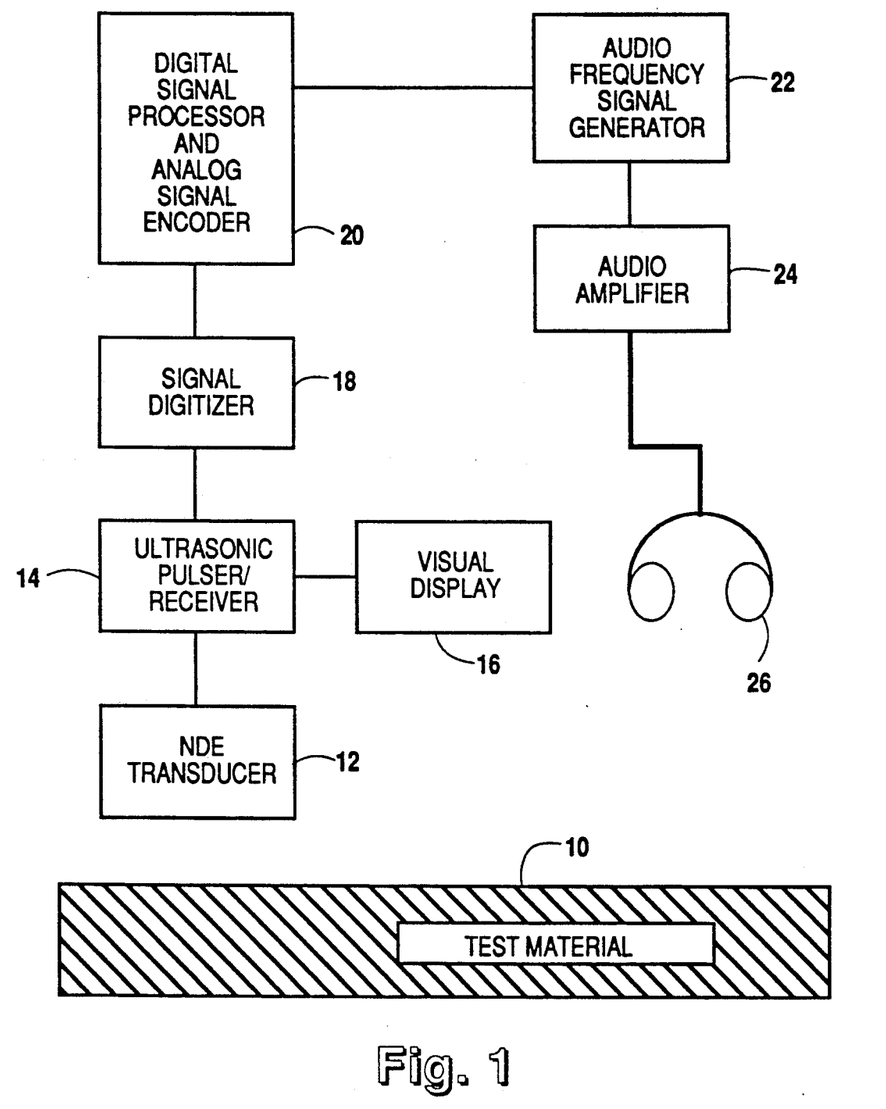
FIG. 1 is a block diagram of the essential components of the apparatus of the present invention.

Reference is made first to FIG. 1 for a detailed description of the components of a system appropriately configured to implement the method of the present invention. Test material 10, which is to undergo non-destructive evaluation is positioned f or access by the system components. Specifically, non-destructive evaluation (NDE) transducer 12 is placed in contact or near contact with test material 10. NDE transducer 12 may transmit and/or receive an inspection signal of an acoustic or electromagnetic character predetermined to elicit the type of information desired from test material 10. NDE transducer 12 is connected to and controlled by transmitter/receiver 14. Transmitter/receiver 14 both generates the signal that is transmitted by NDE transducer 12, and receives a return signal from NDE transducer 12. In a preferred embodiment, transmitter/receiver 14 is configured to transmit and receive ultrasonic waveforms, but in alternate embodiments could be configured to transmit and receive a range of sonic or electromagnetic wave forms. Transmitter/receiver 14 performs a certain amount of immediate information interpretation by working in conjunction with NDE transducer 12 to convert the ultrasonic or electromagnetic wave forms received into electrical signals. These electrical signals may be appropriately conditioned and immediately displayed on visual display 16.

Visual display 16 in the preferred embodiment may be a conventional oscilloscope type device with integral or external synchronization capable of displaying amplitude, frequency, and time values associated with standard ultrasonic NDE transducers. Other forms of transmitted and received waves may require further signal conditioning prior to being displayed on a monitor.

Up to this point in the system, the present invention differs little from the methods envisioned by the prior art. In the prior art, an operator typically utilized a hand held transducer similar to NDE transducer 12, and positioned it over test material 10 while visually tracking the characteristics of test material 10 on a visual display such as display 16. The present invention adds to, or in some cases replaces, the utilization of a visual display for the interpretation of the information required by the test operator. In addition to providing signal information to visual display 16, transmitter/receiver 14 provides signal information to signal digitizer 18. signal digitizer 18 takes the analog signal information representing frequency, amplitude, and time, and encodes this information into digital form. Once digitized, this information can be analyzed and correlated with predetermined operational reference standards.

Under some situations and with certain applications, it may be more appropriate to utilize an analog signal processor rather than signal digitizer 18. It is possible that taking the analog signal information and converting it into a second analog signal that can be analyzed and correlated with the appropriate audio output characteristics, could be more practical in so-me instances. The important step in the process is the encoding of the signal information representing frequency, amplitude, and time, into a form that can be analyzed and correlated with what previous tests have already shown to be appropriate aural reference standards. Thus while this description of a preferred embodiment addresses the analysis of the signal information in digital form, it is expected that a similar analysis could occur with the signal information still in analog form.

Once digitized, the frequency, amplitude, and time information is provided to a digital signal processor and analog signal encoder 20. The digital signal processor component of processor/encoder 20 examines the characteristics of the digitally encoded values for frequency, amplitude, and time, and may determine the most appropriate acoustic signal characteristics to provide to the test operator for accurate interpretation of the information. The digital signal processor may be preprogrammed to choose among a variety of acoustic characteristics, including pitch, loudness, damping, direction, duration, repetition, and rest. The correlations made by digital signal processor 20 should be familiar to the test operator so that their presentation immediately triggers an association with a particular characteristic of test material 10. A given value for test signal amplitude provided by signal digitizer la may, for example, correspond to a pre-determined frequency of audio signal to be generated. The digital signal processor identifies and correlates a digital test signal amplitude value with a specific audio frequency value.

It may also be appropriate to allow the test operator to individually select the specific acoustic signal characteristics to be matched to the encoded values f or frequency, amplitude, and time, that the operator expects to receive. The process of correlating encoded values with acoustic signal characteristics could, therefore, be achieved based upon preprogrammed correlations, test operator preferences, or upon a combination of both.

NDE test signals which quickly repeat in time, for example, may be correlated to a corresponding auditory pitch value, or may involve conversion to an auditory signal with an amplitude proportional to the test signal repetition rate. The range of correlation possibilities is very large and a select group is summarized in Table 1. Table 1 cross references the amplitude, frequency, and time characteristics of the test signal from signal digitizer 18 to the potential acoustic audio characteristics selected in digital signal processor 20. Whereas any of the test signal characteristics conceivably could be correlated to any of the available audio characteristics, there are, as might be expected, certain correlations which provide the most rapid and the most accurate interpretations by the human operator. Such typical correlations are indicated in Table 1.

TABLE 1

| TYPICAL TEST SIGNAL/AUDIO CORRELATIONS | | | |
|---|---|---|---|
| Audio | Test Signal Characteristic | | |
| Characteristic | Amplitude | Frequency | Time |
| Pitch | • | • | |
| Loudness | • | • | • |
| Damping | • | | • |
| Direction | | | • |
| Duration | | | • |
| Repetition | | • | |
| Rest | | | • |

Once digital signal processor 20, or the test operator, has established the appropriate correlations of the incoming calibration test signal values with outgoing auditory signal characteristics, the analog signal encoder portion of processor/encoder 20 encodes the quantitative or qualitative signal characteristics associated with the incoming test signal into corresponding values for auditory signal characteristics. These auditory signal characteristics are then provided to audio frequency signal generator 22. Signal generator 22 receives the encoded signal information, which determines the audio signal characteristics, and generates electrical signals, which when passed through matched audio amplifier 24 and audio sound equipment 26, will provide the characteristics desired. Signal generator 22 provides electrical signals, which will generate acoustic waves through audio sound device 26 that exhibit the amplitude, frequency, time, and spatial characteristics that can be perceived by the operator as specific pitch, loudness, damping, direction, duration, repetition, and rest that have been determined to be appropriate for the particular information being analyzed. Audio amplifier 24 receives the electrical signals from signal generator 22, and amplifies and conditions them to be appropriately broadcast by audio sound device 26. Audio sound device 26 is typically a set of audio ear phones, or in some situations may be discrete audio speaker units. It is important in many applications of the preferred embodiment, that audio sound device 26 be capable of providing spatial sound information by functioning with one or more channels of broadcast. It is anticipated that in some specialized situations, multi channel broadcast might provide an even more accurate means for the operator to interpret the information about test material 10.

Reference is now made to FIGS. 2 and 3 for a description of one application of the method of the present invention. In FIG. 2 NDE transducer 30 is connected to transmitter/receiver (not shown) by electrical conductor 32. Transducer 30 is placed in contact with surface 34 of test material 10. In this configuration, utilizing standard ultrasonic techniques (or other NDE techniques in other applications), transducer 30 may be controlled so as to transmit ultrasonic signals 36 and 37 into test material 10. These signals 36 and 37 encounter material anomaly 40 and are scattered and reflected back to transducer 30 as reflected/generated signals 38 and 39. These reflected/generated signals 38 and 39 are picked up by transducer 30, and converted to electrical signals for further conversion and processing. In standard acoustic NDE techniques, the characteristics of a material anomaly such as crack 40 in test material 10, can be determined by comparing return signal 38 from the tip of crack 40 with return signal 39 from the base of crack 40. This comparison can be graphically seen in FIG. 3, which is a plot of the amplitude of the signal received by transducer 30 versus time. The reception of return signal 38 is shown as an initial change in amplitude followed by a time period of neutral amplitude before a subsequent change in signal amplitude indicative of the reception of return signal 39 from the base of crack 40. This identifiable time period $\Delta T$ shown in the diagram in its typical visual display format, can by experimentation, be correlated to the length of crack 40 or of its other physical characteristics.

Unique to the present invention, it is this $\Delta T$ value that signal digitizer 18 in FIG. 1 can quantify and provide to digital signal processor and analog signal encoder 20 for conversion into a corresponding audio signal characteristic. In its simplest implementation, encoder 20 may provide the signal, reduced in frequency to audible values, for direct playback by the audio equipment. The $\Delta T$ value is thus audibly perceived by the test operator as distinct, time separated, acoustic pulses.

FIG. 4 describes a second type of standard ultrasonic NDE method, which utilizes an NDE transducer similar to that shown in FIG. 2. NDE transducer so is used to determine material thicknesses in test material 10. Transducer So is placed upon surface 48 of test material 10, and is moved through various positions A, B, and C, which correspond to variations in the thickness of test material 10. At position A, transducer 50 transmits an ultrasonic signal 58, which encounters back wall 52 of test material 10, and is reflected back as reflected signal 59. Likewise, when transducer 50 is in position B, transmitted signal 60 is reflected back from back wall 54 as reflected signal 61. In the same way, when transducer So is in position C, transmitted signal 62 is reflected back from back wall 56 as reflected signal 63. The time differential between the transmitted signals 58, 60, and 62, and their corresponding reflected signals 59, 61, and 63 is indicative of the thickness of material 10 at that position. This is graphically represented in FIG. 5, wherein the signal amplitude in each position is displayed over time in its typical visual display format. The signal from position A indicates a specific time delay before reflected signal 59 is received by transducer 50. This time duration $\Delta T_A$ is quantifiable. Similarly, reflected signal 61 at position B has a characteristic time duration before the signal is received by transducer 50. This quantifiable time value is indicated in FIG. 5 as $\Delta T_B$. And finally, the same can be said for the transmitted and received signal at position C, where $\Delta T_C$ is the quantifiable time duration value f or the rejection of transmitted signal 62 as reflected signal 63. Unique to the present invention, these values f or time duration are quantified and digitized by signal digitizer 18, and are provided to processor/encoder 20 for correlation with an appropriate set of audio characteristics. In a preferred embodiment, the test operator might be moving transducer so across surface 48 of test material 10, and be receiving in head phones 26 audio signals of varying pitches that are correlated to the thicknesses of the material beneath the transducer 50 at that point. Transducer 50 in position A may, for example, result in an audio signal of a medium pitch, whereas when moved to position B it might result in an audio signal of a higher pitch indicating a thinner test material 10. Likewise, when moved to position C, transducer 50 might provide information which would result in an audio signal of lower pitch indicating a greater thickness for material 10 at that point.

Figure 6:
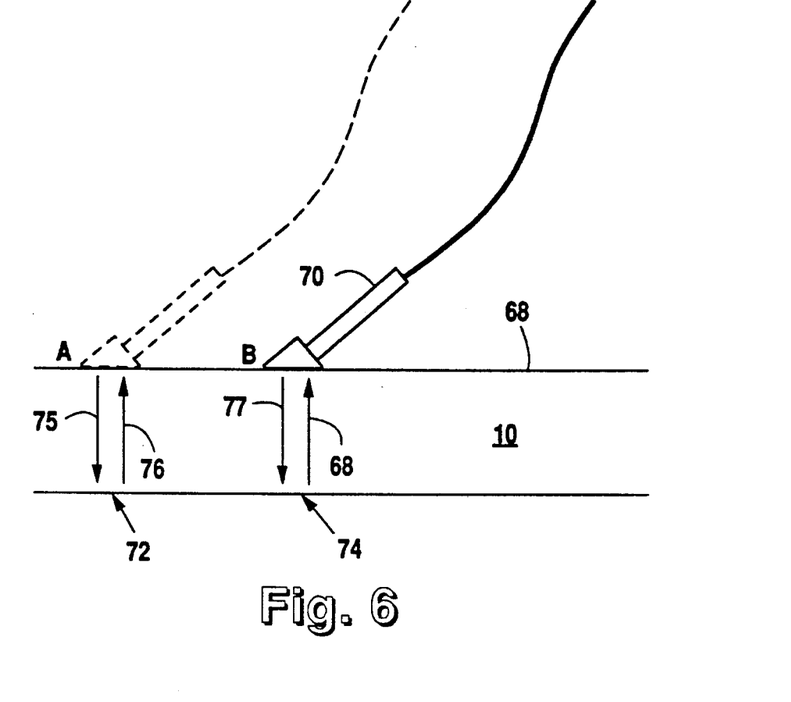
FIG. 6 is a schematic diagram of a prior art ultrasonic method of determining internal wall or interlamination corrosion.
Figure 7:
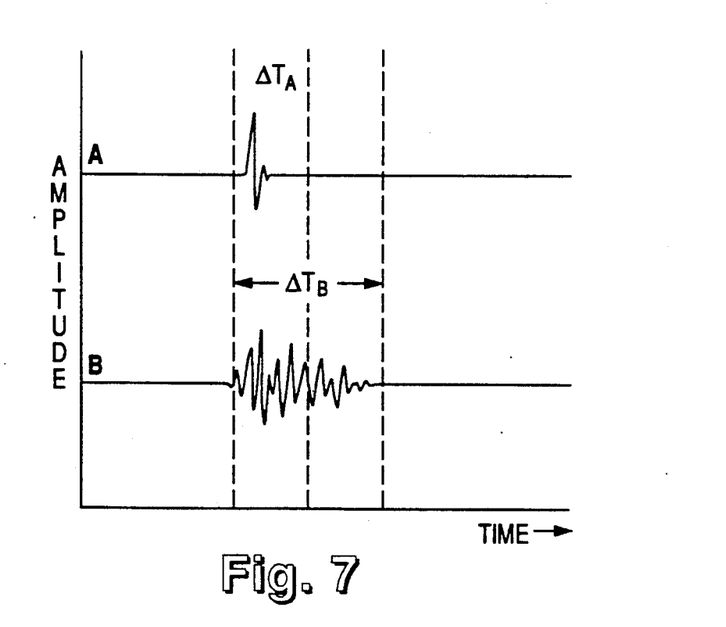
FIG. 7 is a typical display of visual information provided by the ultrasonic method shown in FIG. 6.

In a third standard NDE method shown in FIG. 6, a transducer 70, similar to those described in FIGS. 2 and 4, may be moved across the surface 68 of test material 10 that is known to contain delaminations and/or corrosion on an interior non-exposed surface 73. Non-corroded surface 72 and corroded surface 74 will produce distinct reflections of ultrasonic signals. In position A, transducer 70 transmits ultrasonic signal 75, which encounters back wall 73 at point 72. Point 72, being non-corroded, reflects back a characteristic signal 76 received by transducer 70. Likewise, when in position B, transducer 70 transmits ultrasonic signal 77, which is reflected by corroded point 74 on back wall 73 and reflects back a characteristic signal 78 to be received by transducer 70. The characteristics of these reflected signals are shown graphically in FIG. 7, wherein signal amplitudes and time are displayed. In position A, the signal amplitude of reflected signal 76 is shown to extend over a relatively short period of time $\Delta T_A$. This short amplitude disruption is indicative of a "clean" interior surface. Signal B on the other hand, while it occurs at relatively the same time from the transmission of the signal, has an amplitude disruption that is spread out is over a greater time interval $\Delta T_B$. This greater time of disruption is indicative of a corroded or uneven interior wall surf ace 74 in FIG. 6. It is this $\Delta T_A$ and $\Delta T_B$ that are provided in quantitative digitized form to digital signal processor and analog signal encoder 20 to be correlated with appropriate audio signal characteristics. In this case, pitch or duration might be the most appropriate characteristic to be correlated with surf ace condition. Even though all examples shown herein are related to a $\Delta T$ measurement, this is only one of the signal features which may be presented in an audible format in the present invention.

Figure 8:
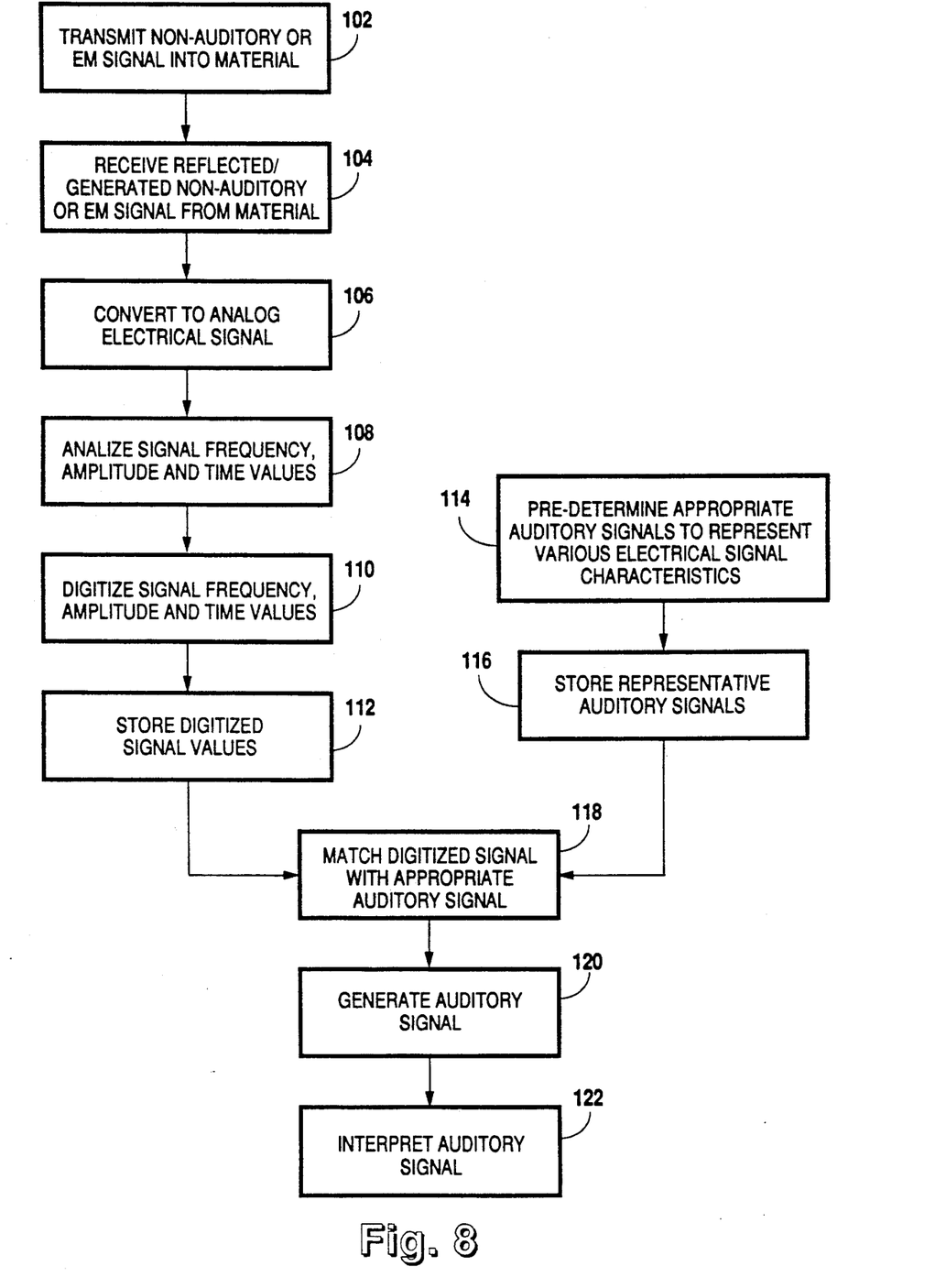
FIG. 8 is a block diagram of the sequence of steps of the method of the present invention.

Reference is now made to FIG. 8 for a description of the sequence of steps of a preferred embodiment of the present invention. Initial step 102 is to transmit the non-auditory or electromagnetic signal into the material under evaluation. Step 104 is the reception back of reflected and generated signals from the material, including those evidencing anomalies, etc. Step 106 is the process of converting this transducer signal into an analog electrical signal. Step 108 is the process of analyzing the electrical signal for characteristic frequency, amplitude and time values. Step 110 is to digitize the signal characteristics for easy correlation and step 112 is to store these signal characteristics so that they might be compared to predetermined patterns.

Step 114 is a preliminary step that provides a history of appropriate auditory signals that are chosen to represent and/or track the various electrical signal characteristics. Step 116 is also a preliminary step of storing these representative auditory signals. Step 118 is the process of comparing the stored digitized signal with the stored patterns and selecting an appropriate representative or tracking auditory signal. Finally, step 120 is the process of generating the auditory signal for the human ear to receive, and step 122 is the interpretation of that signal by the listener.

As mentioned previously, ultrasonic NDE technologies are used in the preferred embodiment of the present invention only because they are some of the most commonly applied NDE technologies, and because they are representative of all such technologies that could just as easily utilize the devices and methods of the present invention. The detection of radio waves, microwaves, eddy currents, and even visual light waves as they are transmitted through test materials, lend themselves to the techniques and devices of the present invention. Essentially, any NDE information that is transmitted by way of waves or fields whose flux, frequency, density, amplitude, and time properties can be described lends itself to the application of the present invention.

One important aspect of the implementation of the present invention is the education of the test operator to the correlations between test material characteristics and auditory characteristics. Just as with any visual display, some reference must be created for the test operator to associate a particular auditory or visual event with a particular physical characteristic of the test material. The implementation of the present invention is, therefore, a two step process. Not only must a set of references be created that optimally associate physical characteristics of test materials with auditory sound characteristics, but these references must be firmly established in the operator's mind so that their occurrence is rapidly interpreted as indicating the existence of the particular test material characteristic. Once such an educational process has occurred, however, the ability of the human auditory system to interpret this information equals or surpasses the ability of the human optical system to interpret similarly presented visual information.

The proper correlation to achieve optimal interpretive capabilities is best determined by experimentation. While certain parameters of the acoustic behavior that is presented to the test operator are defined by the limitations of the human auditory system, for example the range of frequencies and amplitudes, the finer distinctions associated with pitch, repetition, and the other acoustic parameters mentioned are not so thoroughly understood as to lend themselves to correlation without experimentation. Table 1 presented above summarizes the results of the experimentation to date, and identifies those correlations that appear to provide easily interpretable acoustic information to the test operator.

While the foregoing discussion of the present invention has described a method and an apparatus in relation to certain preferred embodiments, and specific details have been disclosed for the purpose of illustration, it will be apparent to those skilled in the art that the invention is open to additional embodiments and that the details of the descriptions above could be altered considerably without departing from the basic principles of the invention.

I claim:

1. A method for using the abilities of the human auditory system to interpret information about, and to identify, characteristics of a material under analysis, comprising the steps of:

sensing acoustic and/or electromagnetic conditions in said material, said conditions being indicative of said characteristics of said material;

creating an electrical signal of said acoustic and/or electromagnetic conditions, said electrical signal having:

(a) a frequency proportional to frequency characteristics of said acoustic and/or electromagnetic conditions;

(b) an amplitude proportional to amplitude characteristics of said acoustic and/or electromagnetic conditions; and (c) timing correlated to said acoustic and/or electromagnetic conditions;

measuring and storing values for said frequency, amplitude, and timing of said electrical signal;

identifying patterns in said frequency, amplitude, and timing values by comparing to previously identified patterns of frequency, amplitude, and timing values determined through prior experimentation to be produced by specific material characteristics;

creating an acoustic signal pre-selected to be associated with said identified patterns of frequency, amplitude and timing values; and transmitting said acoustic signal to a human listener, wherein said listener has been trained to associate said acoustic signal with said specific material characteristics.

2. The method of claim 1, wherein said step of identifying patterns in said frequency, amplitude, and timing values comprises the steps of:

storing said previously identified patterns of frequency, amplitude, and timing values known to be produced by specific material characteristics;

storing information for generating acoustic signals selected to be associated with said previously identified patterns;

selecting at least one of said stored previously identified patterns;

comparing said measured and stored values for said frequency, amplitude, and timing of said electrical signal, with each of said selected stored patterns;

matching said measured and stored values for said frequency, amplitude, and timing of said electrical signal, with at least one of said selected stored patterns;

selecting said stored information for generating acoustic signals, said information associated with said matched, selected stored patterns;

wherein said selected stored information is capable of generating an acoustic signal recognizable to an observer as being associated with said specific material characteristics.

3. The method of claim 1, wherein said step of creating an acoustic signal comprises creating a signal with variations in at least one of a plurality of sound characteristics consisting of pitch, loudness, damping, direction, duration, repetition, and rest, in an arrangement preselected to be associated with said identified patterns of frequency, amplitude, and timing values.

4. The method of claim 1, wherein said step of transmitting said acoustic signal to a human listener comprises providing at least two channels of said acoustic signal, wherein said channels are capable of providing signal information to said human listener.

5. The method of claim 1 further comprising the steps of converting said electrical signal indicative of said acoustic and/or electromagnetic conditions into a visually perceptible graphic display having characteristics correlated to said electrical signal.

6. A method for using the abilities of the human auditory system to interpret information about, and to identify, characteristics of a material under analysis, comprising the steps of:
transmitting acoustic and/or electromagnetic waves into said material;
receiving reflected and generated acoustic and/or electromagnetic waves from said material, said reflected and generated waves having characteristics indicative of said characteristics of said material;
creating an electrical signal indicative of said received reflected and generated acoustic and/or electromagnetic waves, said electrical signal having:
(a) a frequency proportional to frequency characteristics of said received acoustic and/or electromagnetic waves;
(b) an amplitude proportional to amplitude characteristics of said received acoustic and/or electromagnetic waves; and
(c) timing correlated to said received acoustic and/or electromagnetic waves;
digitizing values for said frequency, amplitude, and timing of said electrical signal;
storing said digitized values for said frequency, amplitude, and timing of said electrical signal;
identifying patterns in said frequency, amplitude, and time values by comparing to previously identified patterns of frequency, amplitude, and timing values determined through prior experimentation to be produced by specific material characteristics;
creating an acoustic signal pre-selected to be associated with said identified patterns of frequency, amplitude, and time values; and
transmitting said acoustic signal to a human listener; wherein said listener has been trained to associate said acoustic signal with said specific material characteristics.

7. An apparatus for encoding information about characteristics of a material under analysis into auditory acoustic behavior capable of interpretation by the human auditory system, comprising:
means for sensing acoustic and/or electromagnetic conditions in said material, said conditions being indicative of said characteristics of said material;
means for creating an electrical signal indicative of said acoustic and/or electromagnetic conditions, said electrical signal having:
(a) a frequency proportional to frequency characteristics of said acoustic and/or electromagnetic conditions;
(b) an amplitude proportional to amplitude characteristics of said acoustic and/or electromagnetic conditions; and
(c) timing correlated to said acoustic and/or electromagnetic conditions;
means for measuring values of said frequency, amplitude, and timing of said electrical signal;
microprocessor means for storing said measured values for said frequency, amplitude, and timing of said electrical signal, and comparing said measured values to previously stored values of frequency, amplitude, and timing known to be produced by specific material characteristics, said microprocessor means further identifying and correlating patterns in said stored frequency, amplitude, and timing values with similar patterns previously stored and known to be produced by specific material characteristics, said microprocessor means further storing information necessary for the creation of an acoustic signal to be selected from stored information for a plurality of acoustic signals, said stored acoustic signal information associated with said identified patterns of frequency, amplitude, and timing values;
means for creating an acoustic signal preselected to be associated with said identified patterns of frequency, amplitude, and timing values; and
means for transmitting said acoustic signal to a human listener, wherein said listener has been trained to associate said acoustic signal with said specific material characteristics.

8. The apparatus of claim 7, wherein said means for transmitting said acoustic signal to a human listener comprises means for transmitting at least two channels of said acoustic signal.

9. The apparatus of claim 7 further comprising means for converting said electrical signal indicative of said acoustic and/or electromagnetic conditions into a visually perceptible graphic display having characteristics correlated to said electrical signal.

10. The apparatus of claim 7, wherein said means for creating an electrical signal comprises a signal amplifier and a signal generator.

11. The apparatus of claim 7, wherein said means for measuring values of said frequency, amplitude, and timing of said electrical signal comprises an electronic analog to digital converter.

12. The apparatus of claim 7, wherein said means for creating an acoustic signal comprises an audio frequency signal amplifier and at least one audio speaker device.

* * * * *